US012806421B2

(12) United States Patent
Jayakumar et al.

(10) Patent No.: US 12,806,421 B2
(45) Date of Patent: Nov. 24, 2026

(54) CLOSED-LOOP FEATURE OPTIMIZATION OF BIOLOGICAL SIGNALS

(71) Applicant: Boston Scientific Neuromodulation Corporation, Valencia, CA (US)

(72) Inventors: Adarsh Jayakumar, Valencia, CA (US); Robert Sutherland, Alexandria, VA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 802 days.

(21) Appl. No.: 18/085,369

(22) Filed: Dec. 20, 2022

(65) Prior Publication Data

US 2023/0191131 A1 Jun. 22, 2023

Related U.S. Application Data

(60) Provisional application No. 63/292,778, filed on Dec. 22, 2021.

(51) Int. Cl.
*A61N 1/36* (2006.01)
*A61B 5/00* (2006.01)
*G16H 20/30* (2018.01)

(52) U.S. Cl.
CPC ........ *A61N 1/36139* (2013.01); *A61B 5/4836* (2013.01); *A61B 5/7264* (2013.01); *A61N 1/36132* (2013.01); *G16H 20/30* (2018.01)

(58) Field of Classification Search
CPC ............ A61N 1/36139; A61N 1/36132; A61N 1/0534; A61N 1/36062; A61N 1/37235;
(Continued)

(56) References Cited

U.S. PATENT DOCUMENTS 10,071,248 B2 9/2018 Netoff et al.
12,097,029 B1 * 9/2024 Shanechi ............... A61B 5/374
(Continued)

FOREIGN PATENT DOCUMENTS

WO WO-2008109508 A2 * 9/2008 ............. G16H 20/70
WO WO-2013067536 A1 * 5/2013 ......... G01N 33/4905
(Continued)

OTHER PUBLICATIONS

Haddock, Andrew James, et al., "Anomaly Detection for Sensed Electrophysiological Data", U.S. Appl. No. 63/197,612, filed Jun. 7, 2021.
(Continued)

*Primary Examiner* — Jonathan T Kuo
(74) *Attorney, Agent, or Firm* — Schwegman Lundberg & Woessner, P.A.

(57) ABSTRACT

A system may include a therapy device configured to deliver a therapy to a patient, a feature detector, and a feature selection controller. The therapy device may include sensing circuitry configured to sense a biological signal from the patient, and a closed-loop controller operably connected to the therapy device and the sensing circuitry. The controller may be configured to implement a feedback control algorithm to control the delivered therapy based on the sensed signal by controlling at least one therapy parameter. The feature detector may be configured to detect a plurality of available features of the biological signal. The feature selection controller may be configured to implement a feature selection algorithm to determine closed-loop sensed feature(s) from the plurality of available features. The feedback control algorithm may be configured to use the at least one closed-loop sensed feature to control the therapy parameter(s).

20 Claims, 7 Drawing Sheets

(58) Field of Classification Search
CPC .. A61N 1/36031; G16H 20/30; A61B 5/4836; A61B 5/72–5/7296
See application file for complete search history.

(56) References Cited

U.S. PATENT DOCUMENTS

| | | | |
|---|---|---|---|
| 2018/0178013 A1 | 6/2018 | Bouton et al. | |
| 2020/0108253 A1 | 4/2020 | Crowder et al. | |
| 2021/0069512 A1 | 3/2021 | Moffitt et al. | |
| 2021/0252287 A1 | 8/2021 | Esteller et al. | |
| 2022/0215948 A1 * | 7/2022 | Bardot | G16H 40/40 |
| 2022/0355112 A1 | 11/2022 | Weiss et al. | |

FOREIGN PATENT DOCUMENTS

| | | | | |
|---|---|---|---|---|
| WO | WO-2016000035 A1 * | 1/2016 | | G06F 17/00 |
| WO | WO-2016196790 A1 * | 12/2016 | | A61B 5/726 |
| WO | WO-2023122083 A1 | 6/2023 | | |

OTHER PUBLICATIONS

Sand, Daniel, et al., “Machine learning-based personalized subthalamic biomarkers predict ON-OFF levodopa states in Parkinson patients”, J Neural Eng. May 17, 2021;18(4). doi: 10.1088/1741-2552/abfc1d.
“European Application Serial No. 22854253.6, Response to Communication Pursuant to Rules 161 and 162 filed Jan. 29, 2025”, 10 pgs.
“International Application Serial No. PCT/US2022/053498, International Preliminary Report on Patentability mailed Jul. 4, 2024”, 8 pgs.
“International Application Serial No. PCT/US2022/053498, International Search Report mailed Mar. 23, 2023”, 4 pgs.
“International Application Serial No. PCT/US2022/053498, Written Opinion mailed Mar. 23, 2023”, 6 pgs.

* cited by examiner

CLOSED-LOOP FEATURE OPTIMIZATION OF BIOLOGICAL SIGNALS

CLAIM OF PRIORITY

This application claims the benefit of U.S. Patent Application Ser. No. 63/292,778, filed on Dec. 22, 2021, which is hereby incorporated by reference in its entirety.

TECHNICAL FIELD

This document relates generally to medical systems, and more particularly, but not by way of limitation, to systems, devices, and methods for selecting or optimizing a biological signal feature used to provide a closed-loop therapy.

BACKGROUND

Therapy devices are devices configured to deliver a therapy. These devices may be external or implantable. Examples of therapy devices include electrical therapy devices such as neuromodulators and cardiac rhythm management devices, mechanical therapy devices, thermal therapy devices, and drug delivery devices. Examples of neuromodulators include, but are not limited to, spinal cord stimulators (SCS), deep brain stimulators (DBS), peripheral nerve stimulation (PNS) and function electrical stimulation (FES). Examples of cardiac rhythm management device include, but are not limited to, pacemakers and defibrillators. Examples of mechanical devices include, but are not limited to, devices configured to deliver compression to prevent deep vein thrombosis or to massage fluid from legs. Examples of drug delivery devices include, but are not limited to, insulin pumps or other infusion pumps.

With respect to neuromodulators, for example, an external programming device may be used to program the implantable neurostimulator with modulation parameters controlling the delivery of the neuromodulation energy. For example, modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y).

Conventionally, the customization of values for these parameters to a patient can be very time costly. For example, the modulation parameters may be configured as a neuromodulation program capable of being implemented by the neuromodulator, and the neurostimulator may be programmed with more than one program. In order to find a program that provides an effectively provides a therapy (e.g., pain relief) with negligible side effects, the patient or clinician may implement different programs within the neuromodulator.

Sensing electrophysiological data while providing neuromodulation therapy provides a plausible closed-loop feedback mechanism by which to regulate the therapy. For example, closed-loop algorithms for SCS and DBS may use extracted features from a biological system to update therapy. As the optimal feature-therapy relationships may vary from patient to patient, it is desirable for the extracted feature(s) to be personalized for a given patient for ideal closed-loop performance. However, this personalization process can be burdensome to perform manually. A training period prior to functioning in closed-loop mode may be used determine the relationships between extracted features and stimulation therapy. However, environmental effects, such as lead migration, impedance changes, scar tissue formation, disease progression, and other disturbances, such as electromagnetic interference (EMI) events, on both short-time and long-time scales can alter the relationship between the neuromodulation parameters and extracted features. These effects can render the training data outdated causing the closed-loop algorithms to become less effective.

Therefore, there is a need to improve closed-loop therapy.

SUMMARY

An example (e.g., "Example 1") of a system may include a therapy device configured to deliver a therapy to a patient, a feature detector, and a feature selection controller. The therapy may be at least partially defined by a set of therapy parameters. The therapy device may include sensing circuitry configured to sense a biological signal from the patient, and a closed-loop controller operably connected to the therapy device and the sensing circuitry. The controller may be configured to implement a feedback control algorithm to control the delivered therapy based on the sensed electrical signal by controlling at least one therapy parameter from the set of therapy parameters. The feature detector may be configured to detect a plurality of available features of the biological signal. The feature selection controller may be configured to implement a feature selection algorithm to determine at least one closed-loop sensed feature from the plurality of available features. The feedback control algorithm may be configured to use the at least one closed-loop sensed feature to control the at least one therapy parameter.

In Example 2, the subject matter of Example 1 may optionally be configured such that the therapy device is configured to be implantable and is further configured to deliver a neuromodulation therapy to the patient.

In Example 3, the subject matter of any one or more of Examples 1-2 may optionally be configured such that the feature detector includes at least one of a firmware-implemented feature detector or a software-implemented feature detector.

In Example 4, the subject matter of any one or more of Examples 1-3 may optionally be configured such that the therapy device includes the feature detector configured to detect the plurality of available features.

In Example 5, the subject matter of any one or more of Examples 1-4 may optionally be configured such that the therapy device includes the feature selection controller.

In Example 6, the subject matter of any one or more of Examples 1-5 may optionally be configured such that the feature selection algorithm implemented by the feature selection controller is configured to use feedback from a healthcare provider to determine the at least one closed-loop sensed feature from the plurality of available features. The healthcare provider may include physicians, nurses, clinical reps, or others who are qualified to administer healthcare using the therapy device.

In Example 7, the subject matter of any one or more of Examples 1-6 may optionally be configured such that the feature selection algorithm implemented by the feature selection controller is configured to use feedback from patient to determine the at least one closed-loop sensed feature from the plurality of available features.

In Example 8, the subject matter of any one or more of Examples 1-7 may optionally be configured such that the feature selection algorithm implemented by the feature selection controller is configured to use sensed data to determine the at least one closed-loop sensed feedback feature from the plurality of available features.

In Example 9, the subject matter of Example 8 may optionally be configured such that the sensed data used to determine the at least one closed-loop sensed feature includes at least one of the plurality of available features, and the feature selection algorithm implemented by the feature selection controller is configured to determine when the at least one of the plurality of available features is out of expected bounds meets or does not meet expected behavior during the delivery of the therapy.

In Example 10, the subject matter of any one or more of Examples 1-9 may optionally be configured such that the feature selection controller is configured to run autonomously within the therapy device to update the at least one closed-loop sensed feature for use by the feedback control algorithm to control the at least one therapy parameter.

In Example 11, the subject matter of Example 10 may optionally be configured such that the feature selection algorithm includes at least one of: F-Statistic Maximization, Lasso Regression, Fast Correlation-Based Filter (FCBF) or Bhattacharyya Distance.

In Example 12, the subject matter of any one or more of Examples 1-11 may optionally be configured such that the feature selection controller is external to the therapy device and is configured to perform a retrospective analysis, in response to a trigger, of previously-recorded data.

In Example 13, the subject matter of Example 12 may optionally be configured such that the trigger includes a user command or a detected feature anomaly during the therapy.

In Example 14, the subject matter of any one or more of Examples 12-13 may optionally be configured such that the feature selection algorithm includes at least one of: MRMR (maximum relevance-minimum redundance), Regularized Decisions Trees, Evolutionary Algorithms, or Quadratic Programming Feature Sections.

In Example 15, the subject matter of any one or more of Examples 12-14 may optionally be configured such that the feature selection algorithm includes at least one of: filter methods, wrapper methods or embedded methods.

Example 16 includes subject matter (such as a method, means for performing acts, machine readable medium including instructions that when performed by a machine cause the machine to performs acts, or an apparatus to perform). The subject matter may include: delivering a therapy to a patient, wherein the therapy is at least partially defined by a set of therapy parameters; sensing a biological signal from the patient; detecting a plurality of available features of the biological signal; implementing a feature selection algorithm to determine at least one closed-loop sensed feature from the plurality of available features; and implementing a feedback control algorithm, using the at least one closed-loop sensed feature, to control at least one therapy parameter in the set of therapy parameters.

In Example 17, the subject matter of Example 16 may optionally be configured such that the therapy includes a neuromodulation therapy.

In Example 18, the subject matter of any one or more of Examples 16-17 may optionally be configured for using at least one of hardware, firmware or ASICs within an implantable device to detect the plurality of available features.

In Example 19, the subject matter of any one or more of Examples 16-18 may optionally be configured for using software to detect the plurality of available features.

In Example 20, the subject matter of any one or more of Examples 16-19 may optionally be configured for using feedback from a healthcare provider to implement the feature selection algorithm to determine at least one closed-loop sensed feature.

In Example 21, the subject matter of any one or more of Examples 16-20 may optionally be configured for using feedback from the patient to implement the feature selection algorithm to determine at least one closed-loop sensed feature.

In Example 22, the subject matter of any one or more of Examples 16-21 may optionally be configured for using sensed data to implement the feature selection algorithm to determine at least one closed-loop sensed feature.

In Example 23, the subject matter of Example 22 may optionally be configured such that the sensed data includes at least one of the plurality of available features, and to further include determining when the at least one of the plurality of available features meets or does not meet expected behavior during the delivery of the therapy.

In Example 24, the subject matter of any one or more of Examples 16-23 may optionally be configured such that the implementing the feature selection algorithm includes autonomously running the feature selection algorithm within an implanted device to update the at least one closed-loop sensed feature for use by the feedback control algorithm to control the at least one therapy parameter.

In Example 25, the subject matter of Example 24 may optionally be configured such that the feature selection algorithm includes at least one of: F-Statistic Maximization, Lasso Regression, Fast Correlation-Based Filter (FCBF) or Bhattacharyya Distance.

In Example 26, the subject matter of any one or more of Examples 16-25 may optionally be configured such that the implementing the feature selection algorithm includes implementing the feature selection algorithm in an external device, in response to a trigger, to retrospectively analyze previously-recorded data.

In Example 27, the subject matter of Example 26 may optionally be configured such that the trigger includes a user command or a detected feature anomaly during the therapy.

In Example 28, the subject matter of any one or more of Examples 26-27 may optionally be configured such that may optionally be configured such that the feature selection algorithm includes at least one of: MRMR (maximum relevance-minimum redundance), Regularized Decisions Trees, Evolutionary Algorithms, or Quadratic Programming Feature Sections.

In Example 29, the subject matter of any one or more of Examples 26-28 may optionally be configured such that the feature selection algorithm includes at least one of: filter methods, wrapper methods or embedded methods.

Example 30 includes subject matter (such as a device, apparatus, or machine) that may include non-transitory machine-readable medium including instructions, which when executed by a machine, cause the machine to perform a method comprising delivering a therapy to a patient, wherein the therapy is at least partially defined by a set of therapy parameters; sensing a biological signal from the patient, wherein the biological signal has a plurality of available features; implementing a feature selection algorithm to determine at least one closed-loop sensed feature from the plurality of available features; and implementing a feedback control algorithm, using the at least one closed-loop sensed feature, to control at least one therapy parameter in the set of therapy parameters.

In Example 31, the subject matter of Example 30 may optionally be configured such that at least one of hardware, firmware or ASICs within an implantable device detects the plurality of available features.

In Example 32, the subject matter of any one or more of Examples 30-31 may optionally be configured to include detecting the plurality of available features.

In Example 33, the subject matter of any one or more of Examples 30-32 may optionally be configured to further include using sensed data to implement the feature selection algorithm to determine at least one closed-loop sensed feature, wherein the sensed data includes at least one of the plurality of available features, and the method includes determining when the at least one of the plurality of available features meets or does not meet expected behavior during the delivery of the therapy.

In Example 34, the subject matter of any one or more of Examples 30-33 may optionally be configured to further include using sensed data to implement the feature selection algorithm to determine at least one closed-loop sensed feature, including autonomously running the feature selection algorithm within an implanted device to update the at least one closed-loop sensed feature for use by the feedback control algorithm to control the at least one therapy parameter.

In Example 35, the subject matter of any one or more of Examples 30-34 may optionally be configured such that the implementing the feature selection algorithm includes implementing the feature selection algorithm in an external device, in response to a trigger, to retrospectively analyze previously-recorded data.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to various processes for choosing which individual or combined extracted features of a biological signal should be used to deliver closed-loop therapy. These selected features may be considered to be the most important features for a model used to develop the closed-loop control algorithm. These processes may run upon a new training data session and/or autonomously throughout product lifetime. The process(es) may be performed iteratively over long (e.g., longer than a few hours, days, weeks, or months) or short (e.g., shorter than a few hours or minutes) periods of time. The process(es) may be performed shortly after implanting the therapy device to initiate the therapy or may be performed sometime later to update the therapy. These features may be classified either through patient, clinical feedback mechanisms or autonomously within the system. The processes may differ in computational speed/efficiency and may be chosen based on the constraints of the system or based on the status of the system such as battery level, therapy settings, and the like. The processes may be performed within the firmware of an implantable device (e.g., implantable neuromodulator) or on an external device. For example, algorithms for autonomous classification may be performed in firmware, or features may be stored in device for later processing and off-chip optimization. For example, the off-chip optimization may be used to provide firmware upgrades that improve the closed-loop therapy. Appropriate selection of the feature(s) for use to provide the closed-loop therapy may use less resources (e.g., battery/power and memory) while maintaining or improving the efficacy of personalized therapy to patient. For example, the most relevant feature(s) should be used while avoiding useless feature(s) and redundant feature(s). While performing the closed-loop therapy, the firmware may provide some randomization for use to select the feature(s) used to provide the closed-loop therapy.

Figure 1:
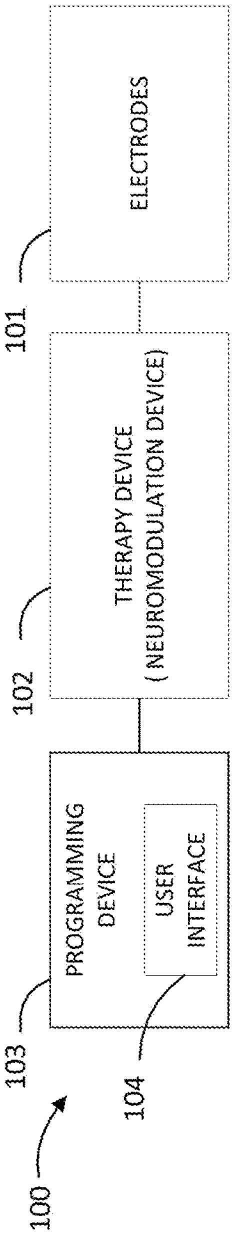
FIG. 1 illustrates, by way of example, an embodiment of a therapy system. The therapy system includes a therapy device is configured to deliver a therapy.

FIG. 1 illustrates, by way of example, an embodiment of a therapy system. The therapy system includes a therapy device is configured to deliver a therapy. The therapy device may be an implantable device or an external device, including wearable devices. Examples of therapy devices include electrical therapy devices such as neuromodulators and cardiac rhythm management devices, mechanical therapy devices, thermal therapy devices, and drug delivery devices. Examples of neuromodulators include, but are not limited to, spinal cord stimulators (SCS), deep brain stimulators (DBS), peripheral nerve stimulation (PNS) and function electrical stimulation (FES). Examples of cardiac rhythm management device include, but are not limited to, pacemakers and defibrillators. Examples of mechanical devices include, but are not limited to, devices configured to deliver compression to prevent deep vein thrombosis or to massage fluid from legs. Examples of drug delivery devices include, but are not limited to, insulin pumps or other infusion pumps. This disclosure discusses neuromodulation systems as an example of a therapy device.

More particularly, FIG. 1 illustrates a neuromodulation system 100 that includes electrodes 101, a neuromodulation device 102 and a programming system such as a programming device 103, which may be or may include a clinician programmer. The programming system may include multiple devices that may be configured to communicate with each other (e.g., remote control, clinician programmer, phone, tablet, and the like). The electrodes 101 are configured to be placed on or near one or more neural targets in a patient. The neuromodulation device 102 is configured to be electrically connected to electrodes 101 and deliver neuromodulation energy, such as in the form of electrical pulses or other waveform, to the one or more neural targets though electrodes 101. The system may also include sensing circuitry to sense a biological signal, which may but does not necessarily form a part of neuromodulation device 102. The delivery of the neuromodulation is controlled using a plurality of modulation parameters that may specify the electrical waveform (e.g., pulses or pulse patterns or other waveform shapes) and a selection of electrodes through which the electrical waveform is delivered. In various embodiments, at least some parameters of the plurality of modulation parameters are programmable by a user, such as a physician or other caregiver. For example, the parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude, pulse width, pulse rate, and burst rate. The programming device 103 enables the user to access the user-programmable parameters, and may also provide the user with data indicative of the sensed biological signal or feature(s) of the sensed biological signal. In various embodiments, the programming device 103 is configured to be communicatively coupled to modulation device via a wired or wireless link. In various embodiments, the programming device 103 includes a user interface 104 such as a graphical user interface (GUI) that allows the user to set and/or adjust values of the user-programmable modulation parameters. The user interface 104 may also allow the user to view the data indicative of the sensed biological signal or feature(s) of the sensed biological signal and may allow the user to interact with that data. The neuromodulation device 102, the programming device 103 and other devices or system may collect data that may be used by the neuromodulation system 100. For example, the user interface 104 may be used to allow the user to answer healthcare-related questions, such as but not limited to the efficacy of the therapy.

The therapy device may provide a closed-loop therapy, in which sensing circuitry is configured for use to detect a biological signal for use to provide feedback. Sensing circuitry may include various components such as an application specific integrated circuit (ASIC), hardware and/or firmware. Sensing circuitry may include software implemented using a processor to further analyze feature(s) of the biological signal. The biological signal may be a measurable signal produced by electrical, chemical or mechanical activity. Examples of electrical signals may include sensing electrical activity in the brain (e.g., EEGs), electrical activity in nerves and muscles (e.g., EMGs), cardiac activity (e.g., ECGs), and other nerve sensing including both non-evoked responses and evoked responses (e.g., evoked compound action potentials (ECAPs) or evoked resonant nerve activity (ERNA)). Examples of mechanical signals may include sounds contractions detected via flex or strain sensors. Examples of chemical signals may include detected analyte concentrations such as glucose and the like. The system may include a feature detector that is configured to detect a plurality of available features of the biological signal. At least one of the features may be used as a closed-loop sensed feature of the biological signal, which may be used by a controller to provide a closed-loop therapy. The closed-loop sensed feature may be compared to a setpoint of that feature, and the difference may be fed into a feedback control algorithm.

Figure 2:
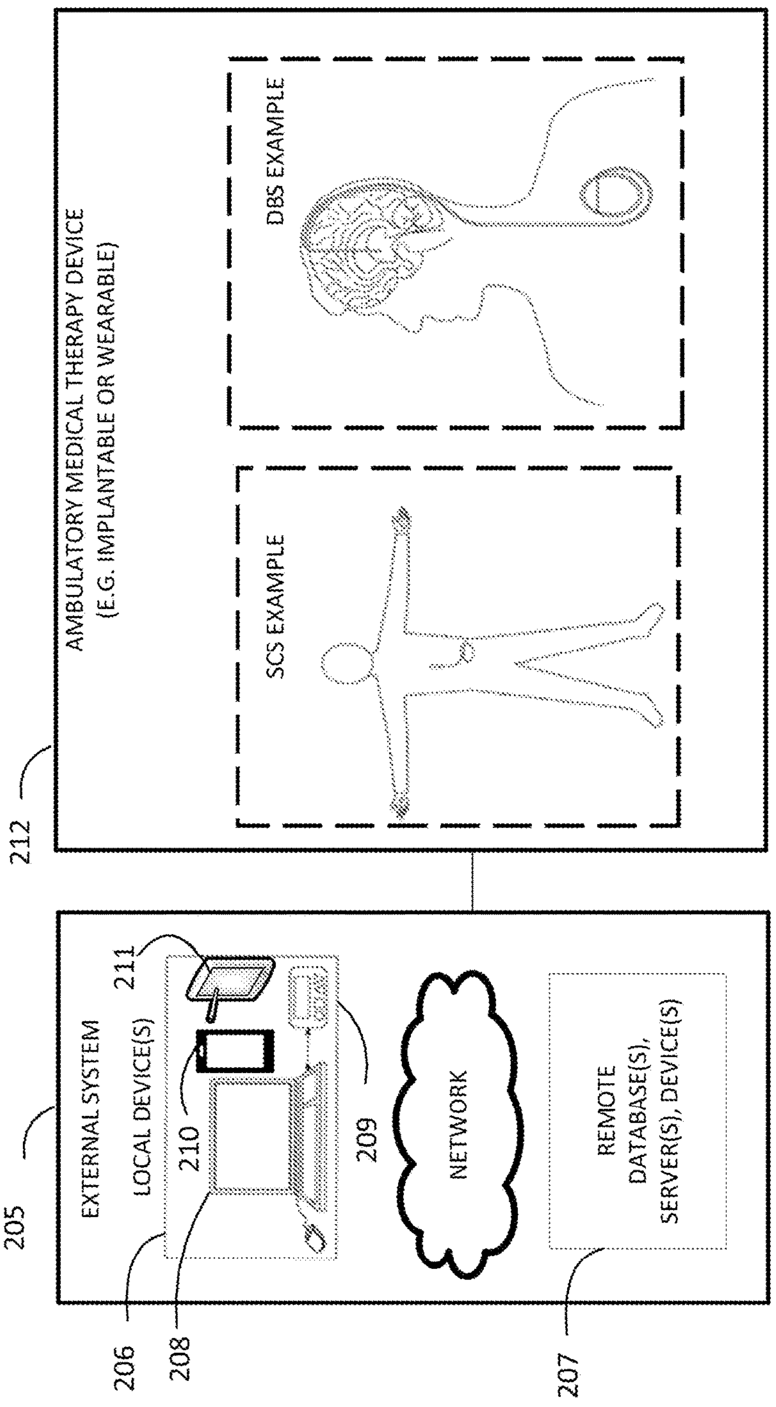
FIG. 2 illustrates, by way of example and not limitation, the neuromodulation system of FIG. 1 implemented in a spinal cord stimulation (SCS) system or a deep brain stimulation (DBS) system.

FIG. 2 illustrates, by way of example and not limitation, the neuromodulation system of FIG. 1 implemented in a spinal cord stimulation (SCS) system or a deep brain stimulation (DBS) system. The illustrated neuromodulation system 200 includes an external system 205 that may include at least one programming device. The illustrated external system 205 may include device(s), at least some of which are configured for use by a clinician to communicate with and program an ambulatory medical therapy device, such as an implantable neuromodulator. Examples of the neuromodulator may include a spinal cord stimulator and deep brain stimulator devices. The external system 205 may include a network of computers, including local device(s) 206 and remote systems 207. The local device(s) 206 may include one or more of a programmer 208, a remote control 209, a phone 210 (e.g., smartphone), and a tablet 211. The remote system 207 may include remote database(s), remote server(s) and remote device(s) capable of communication through the network to local device(s). The external system 205 may be configured for use to program or receive data from the ambulatory therapy device 212. For example, the clinical programmer 208 may be used to program the therapy device 212, using input from remote devices 207 or feedback received from other local devices 206. By way of example and not limitation, the remote control device 207 may allow the patient to turn a therapy on and off and/or may allow the patient to adjust patient-programmable parameter(s) of the plurality of modulation parameters, and the phone 210 or tablet 211 may be used to answer questionnaires to provide input for therapy control. FIG. 2 illustrates a neuromodulation device 202 as an implantable device, although a neuromodulation device 202 may be an external device such as a wearable device. The external system 205 may include a wearables such as a watch, sensors or therapy-applying devices. The watch may include sensor(s), such as sensor(s) for detecting activity, motion and/or posture. Other wearable sensor(s) may be configured for use to detect various physiological parameters such as, but not limited to, activity, motion and/or posture of the patient that may be useful input to control the therapy delivery.

Figure 3:
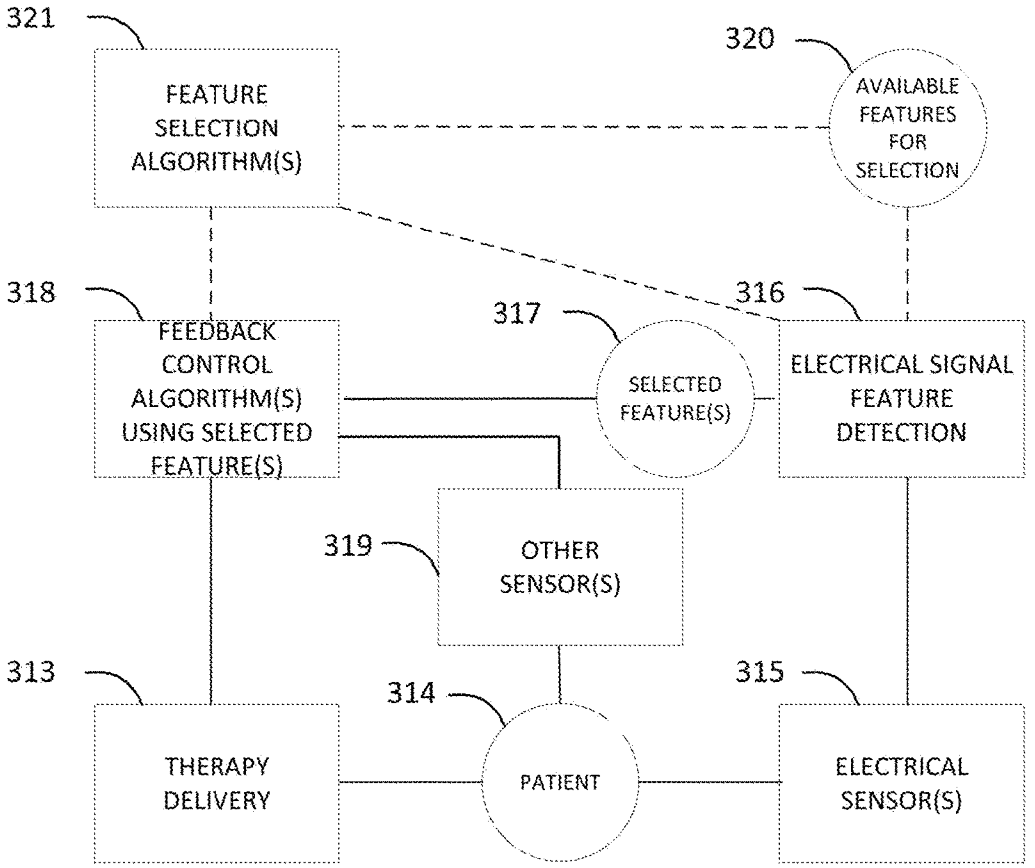
FIG. 3 illustrates, by way of example and not limitation, a closed-loop system that inputs electrical feature(s) into a feedback control algorithm for a therapy, and that further includes feature selection for use to select feature(s) to be input into the feedback control algorithm.

FIG. 3 illustrates, by way of example and not limitation, a closed-loop system that inputs electrical feature(s) into a feedback control algorithm for a therapy, and that further includes feature selection for use to select feature(s) to be input into the feedback control algorithm. The closed-loop system includes a therapy delivery system 313 configured for use to deliver the therapy to a patient 314. For example, where the therapy includes neuromodulation, the therapy delivery may include a waveform generator such as an electrical pulse generator, and electrodes through which the electrical energy is provided to tissue of the patient. Biological sensor(s) may be used to sense biological signal(s) from the patient 314, such as electrical sensor(s) configured to sense electrical signal signal(s). For a neuromodulation system, the electrical sensor(s) may be configured to sense local field potentials (LFPs) or electrical neural activity such as evoked compound action potentials (ECAPs) or evoked resonant neural activity (ERNA), by way of example and not limitation. Feature(s) of the signal may be detected at 316. At least one of the feature(s) may be selected, as illustrated at 317, for use to provide closed-loop therapy. The selected feature(s) may be termed closed-loop sensed feature(s). The closed-loop sensed feature(s) 317 may be input into feedback control algorithm(s) 318 for use to control the therapy. For example, the closed-loop sensed feature may be compared to a setpoint of that feature, and the difference may be fed into a feedback control algorithm. Other sensor(s) 319 may be used to detect other physiological parameter(s) of the patient, which may also be input into the feedback control algorithm(s), which may also be used to control the therapy. For example, the other sensor(s) 319 may detect posture, activity, gait, heart rate, heart rate variability, blood pressure, respiration, oxygen, stress (e.g., galvanic skin response), and the like. The signal feature detection 316 may detect other features 320, which are available to be selected to be implemented as the closed-loop sensed feature(s) fed into the feedback control algorithm(s) 318. A feature selection algorithm 321 may be used to identify the desirable (e.g., "optimized") feature(s) for use to control the therapy. The feature selection algorithm 321 may be used to change the selected feature(s) provided by the feature detection 316 may be change the feedback control algorithm 318. The feature selection algorithm(s) 321 may be implemented on the therapy device (which may be used to provide local optimization described herein) or implemented on external devices (which may be used to provide global optimization described herein). Some embodiments may implement processes to derive new feature(s) to be available for selection for implementation as the closed-loop sensed feature(s).

Figure 4:
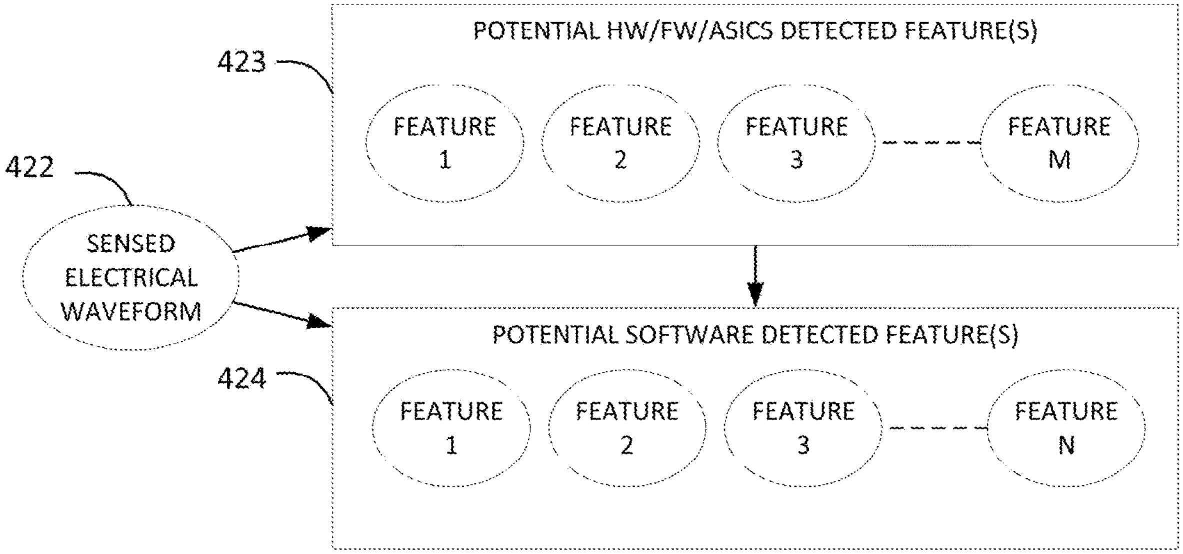
FIG. 4 illustrates, by way of example and not limitation, potential detected features of a sensed electrical waveform.

FIG. 4 illustrates, by way of example and not limitation, potential detected features of a sensed electrical waveform. The sensed electrical waveform (or other biological waveform) 422 may be processed by hardware/firmware/ASICS 423 to detect feature(s) of the waveform, such as "M" features. A feature detector may include both low-level hardware (i.e., ASIC implements feature extraction) and higher-level hardware/firmware (i.e., detection through board-level sensors and code). Any of these features may be available for selection as the closed-loop sensed feature(s). Software 424 may process the sensed waveform 422 and/or one or more of the M features detected by hardware/firmware/ASICs 423 to generate other feature(s) (e.g., "N" features"), any of which may be available for selection as the closed-loop sensed feature(s). Some embodiments may implement a machine learning process enabling the system to detect new feature(s) for analysis as part of the process for optimizing the closed-loop sensed feature(s) to be used for the closed-loop therapy.

Figure 5:
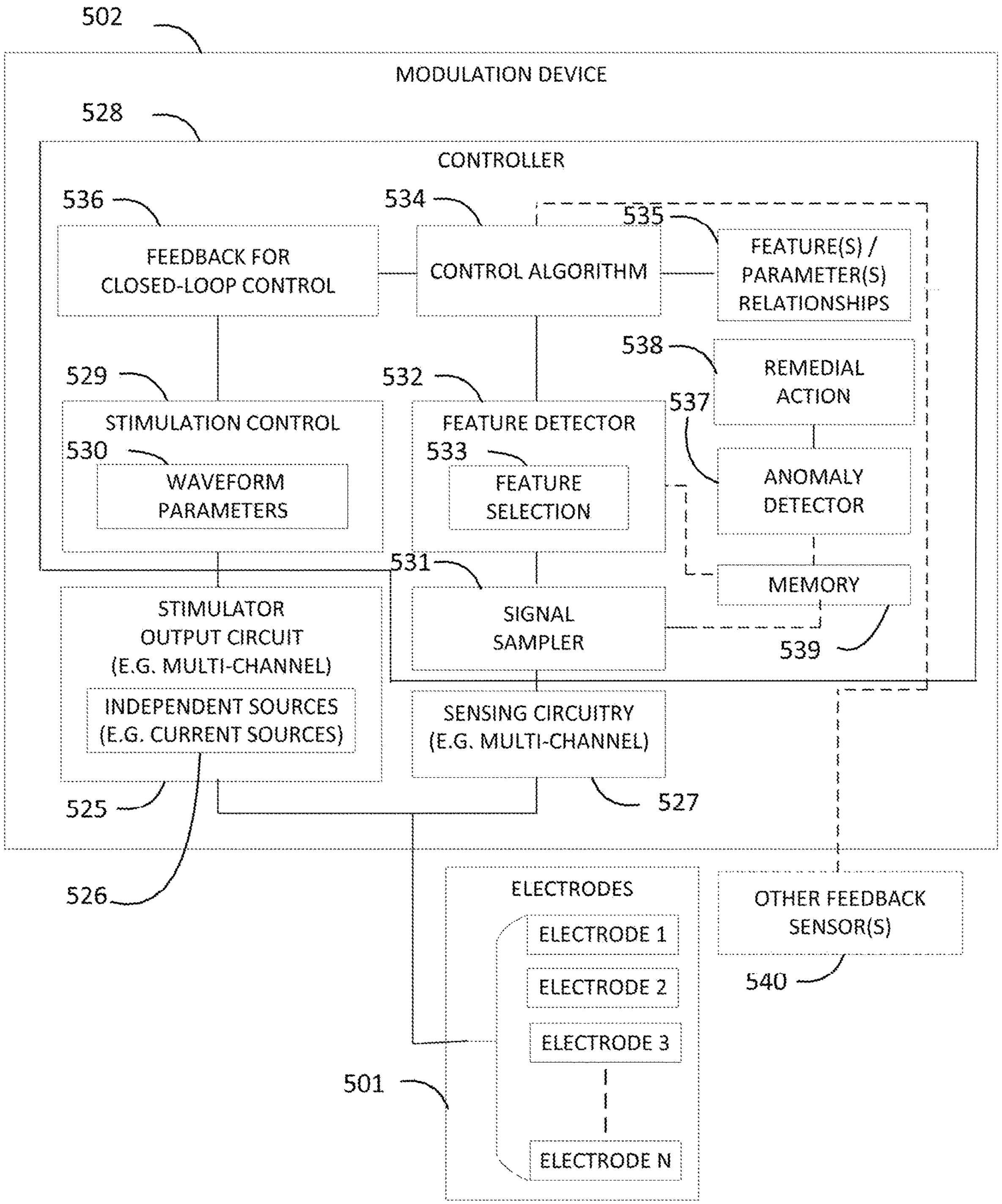
FIG. 5 illustrates, by way of example and not limitation, a modulation device capable of anomaly detection and selecting features of a sensed electrical signal for use to provide feedback for closed-loop control.

FIG. 5 illustrates, by way of example and not limitation, a modulation device capable of anomaly detection and selecting features of a sensed electrical signal for use to provide feedback for closed-loop control. The modulation device 502 is an example of a therapy device illustrated in FIG. 1, and may be configured for use to deliver SCS or DBS therapy, for example. The modulation device 502 may be configured to be connected to electrode(s) 501, illustrated as N electrodes. Any one or more of the electrodes 501 may be configured for use to deliver modulation energy, sense electrical activity, or both deliver modulation energy and sense electrical activity. The modulation device 502 may include a stimulator output circuit 525 configured to deliver modulation energy to electrode(s). The stimulator output circuit 525 may be configured with multiple (e.g., two or more) channels for delivering modulation energy, where each channel may be independently controlled with respect to other channel(s). For example, the stimulator output circuit 525 may have independent sources 526 such as independent current sources or independent voltage sources. The modulation device 502 may include sensing circuitry 527 configured to receive sensed electrical energy from the electrode(s), such as may be used to sense electrical activity in neural tissue or muscle tissue. Other types of therapy devices may sense other types of biological signals (e.g., mechanical or chemical signals). The sensing circuitry 527 may be configured to process signals in multiple (e.g., two or more) channels. By way of example and not limitation, the sensing circuitry 527 may be configured to amplify and filter the signal(s) in the channel(s). Additionally or alternatively, the sensing circuitry may be configured for use with other types physiological sensors, such as but not limited to activity, posture, respiration, heart rate, strain sensors, or analyte sensors.

The modulation device 502 may include a controller 528 operably connected to the stimulator output circuit 525 and the sensing circuitry 527. The controller 528 may include a stimulation control 529 configured for controlling the stimulator output circuit 525. For example, the stimulation control 529 may include start/stop information for the stimulation and/or may include relative timing information between stimulation channels. The stimulation control 529 may include waveform parameters 530 that control the waveform characteristics of the waveform produced by the stimulator output circuit 525. The waveform parameters 530 may include, by way of example and not limitation, amplitude, frequency, and pulse width parameters. The waveform parameters 530 may include, by way of example and not limitation, regular patterns such as patterns regularly repeat with same pulse-to-pulse interval and/or irregular patterns of pulses such as patterns with variable pulse-to-pulse intervals. The waveform parameters may, but do not necessary, define more than one waveform shape (e.g., including a shape other than square pulses with different widths or amplitudes). The stimulation control 529 may be configured to change waveform parameter(s) (e.g., one or more waveform parameters) in response to user input and/or automatically in response to feedback.

The controller 528 may include a signal sampler 531 configured for use to sample a signal produced by the sensing circuitry 527. The controller 528 may further include a feature detector 532 configured to detect one or more features in the sampled signal. A few examples of features that may be detected include peaks (e.g., minimum and/or maximum peaks including local peaks/inflections), range between minimum/maximum peaks, local minima and/or local maxima, area under the curve (AUC), curve length between points in the curve, oscillation frequency, rate of decay after a peak, a difference between features, and a feature change with respect to a baseline. Low-level hardware such as ASICs may extract some features and higher-level hardware/firmware may detect other features through board-level sensors and code. Firmware updates may be used to enable other features to be detected. Software may also be used to detect features. The feature detector may include a feature selection 533 for determining or otherwise providing the selected closed-loop sensed feature. Detected feature(s) from the feature detector 532 may be fed into a control algorithm 534, which may use relationship(s) 535 between the feature(s) and waveform parameter(s) to determine feedback for closed-loop control 536 of the therapy. By way of example, these relationships may be determined using machine learning processes and training data. More than one algorithm may be used to provide the closed-loop control. The algorithm(s) may be selected from a plurality of algorithms that are available to be used to implement the closed-loop control. The different algorithms may use different feature(s) and/or control different waveform parameter(s), and/or have different transfer functions or sensitivity for adjusting the parameter(s) in response to changes in the feature(s). The closed-loop control 536 may be used by the stimulation control 529 to adjust the stimulation (e.g., parameter(s)). The controller 528 of the modulation device 502 may further include an anomaly detector 537 configured to detect anomalies in the feature(s) detected by the feature detector 532. These anomalies may be detected based on the feature data (e.g., training data) used to determine the relationship(s) 535 between the feature(s) and the waveform parameter(s). The controller 528 of the modulation device 502 may further be configured to perform at least some activities for providing remedial action 538 in response to a detected anomaly or detected anomalies. The remedial action may be transitioning from a closed-loop therapy to an open loop therapy, or stopping therapy. The controller 528 may include a memory 539 for storing the detected feature(s) and/or storing the sampled signals, for analysis (e.g., retrospective analysis). The illustrated modulation device 502 may also receive feedback from other sensors 540 as in input into a control algorithm for use to provide feedback for closed-loop control 536.

Figure 6:
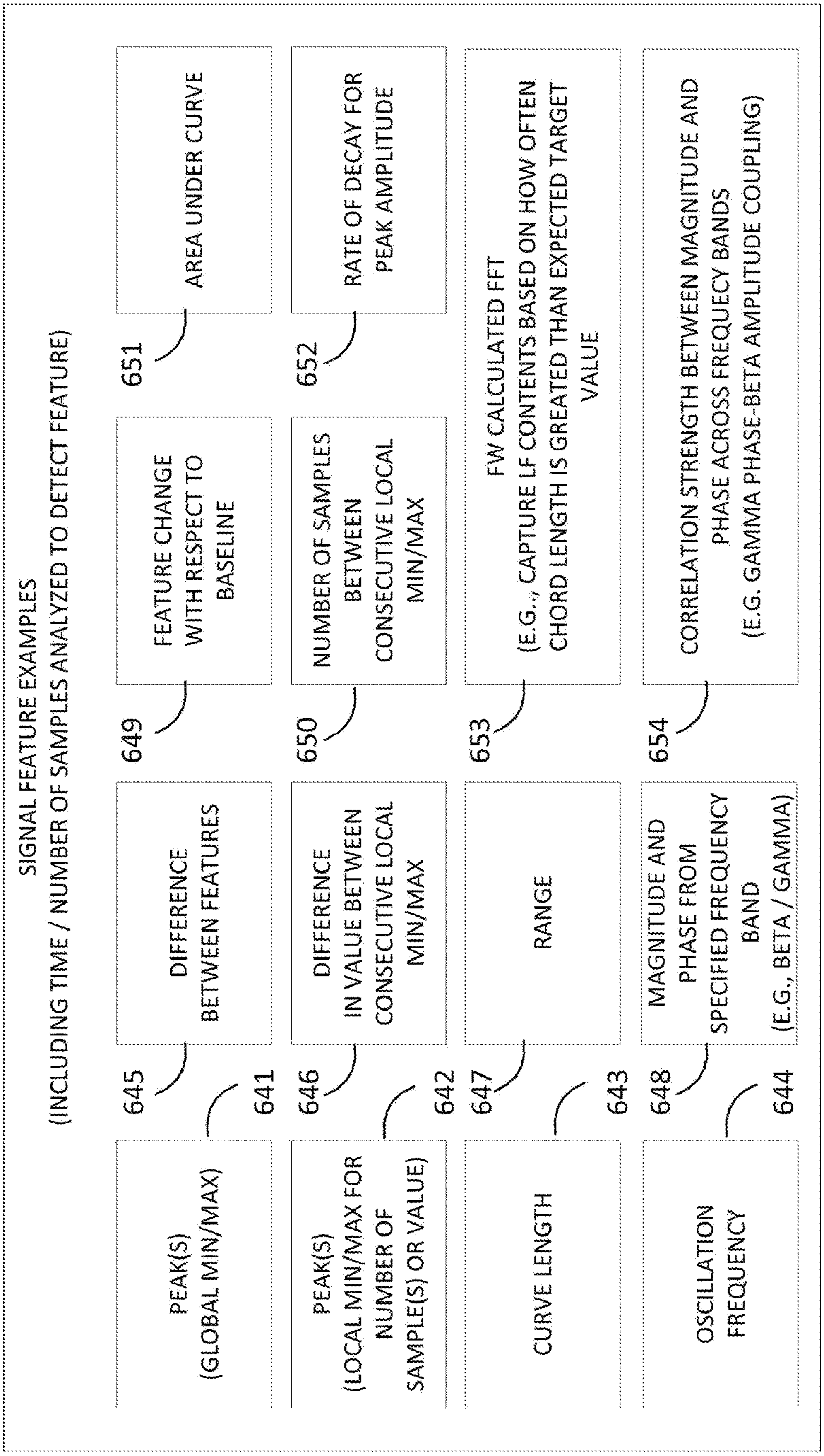
FIG. 6 illustrates, by way of example and not limitation, a few signal features.

FIG. 6 illustrates, by way of example and not limitation, a few signal features. By way of example and not limitation, the feature detection at 316 and 532 in FIGS. 3 and 5, respectively, may be configured to detect a global minimum or maximum value in the signal 641, a local minima or local maxima for the signal over a number of samples or duration 642, a curve length of the signal over a number of samples or duration 643, an oscillation frequency 644, differences between features of the signal 645, differences in value between consecutive local minimums and local maximums 646, a range 647, a magnitude and phase from specified frequency band of signal 648, such as but not limited to the beta and gamma phases, a feature change with respect to a baseline 649, a number of samples or time between consecutive local minimums and maximums 650, an area under the curve 651, a rate of decay for a peak amplitude 652, a firmware calculated Fast Fourier Transform (FFT) 653 that can capture low-frequency contents of signal from how often a chord length is greater than expected target value, and a correlation strength between magnitude and phase across frequency bands of signal 654, such as but not limited to gamma phase-beta amplitude coupling. All features can be calculated within a programmable time bounded window of the total sample data. The time or number of samples to analyze the feature may also be programmed or controlled. A custom ASIC/hardware/firmware is capable of extracting some features. Software is capable of extracting a large number of features.

Figure 7:
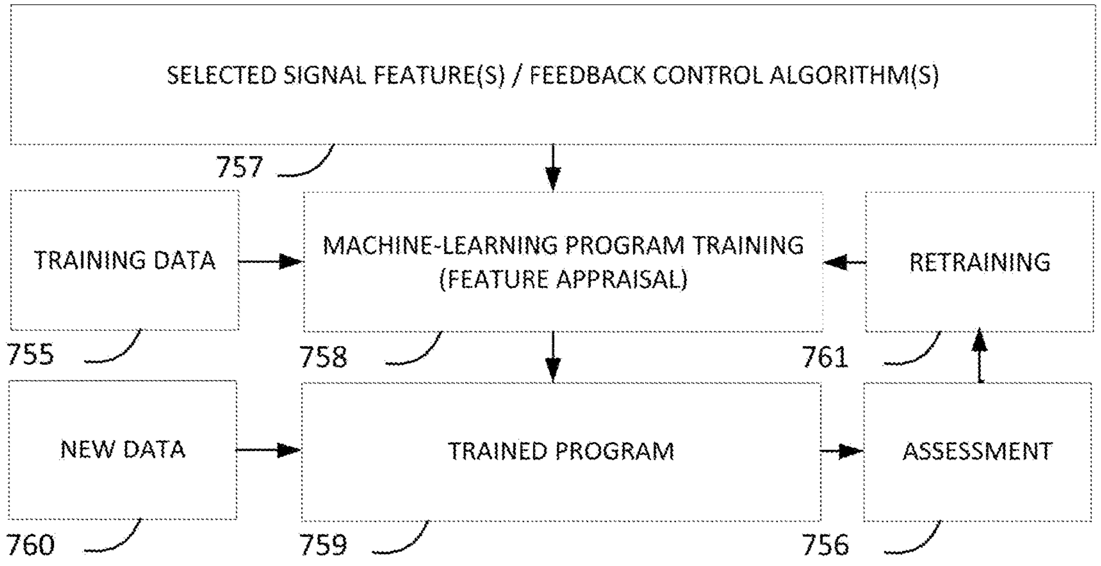
FIG. 7 illustrates, by way of example and not limitation, training and use of a machine-learning program, according to some example embodiments.

FIG. 7 illustrates, by way of example and not limitation, training and use of a machine-learning program, according to some example embodiments. In some example embodiments, machine-learning programs (MLPs), also referred to as machine-learning algorithms or tools, are utilized to perform operations associated with machine learning tasks, such as identifying relationship(s) between detected feature(s) in a sensed biological signal and waveform parameter(s) used to control the neuromodulation. Thus, machine learning may be used to determine the relationships between the extracted features and the simulation therapy referenced in FIGS. 5 and 535.

Machine learning is a field of study that gives computers the ability to learn without being explicitly programmed. Machine learning explores the study and construction of algorithms that may learn from existing data (e.g., "training data") and make predictions about new data. Such machine-learning tools may build a model from example training data 755 in order to make data-driven predictions or decisions expressed as outputs or assessments 756. The machine-learning algorithms use the training data 755 to find correlations among identified features 757 that affect the outcome.

The machine-learning algorithms use features 755 for analyzing the data to generate assessments 756. A feature is an individual measurable property of the observed phenomenon. In the context of a biological signal, some examples of features may include, but are not limited to, peak(s) such as a minimum peak, a maximum peak as well as local minimum and maximum peaks, a range between peaks, a difference in values for features, a feature change with respect to a baseline, an area under a curve, a curve length, an oscillation frequency, and a rate of decay for peak amplitude. Inflection points in the signal may also be an observable feature of the signal, as an inflection point is a point where the signal changes concavity (e.g., from concave up to concave down, or vice versa), and may be identified by determining where the second derivative of the signal is zero. Detected feature(s) may be partially defined by time (e.g., length of curve over a time duration, area under a curve over a time duration, maximum or minimum peak within a time duration, etc.).

The machine-learning algorithms use the training data 755 to find correlations among the identified features 757 that affect the outcome or assessment 756. With the training data 755 and the identified features 757, the machine-learning tool is trained at operation 758. The machine-learning tool appraises the value of the features 757 as they correlate to the training data 755. The result of the training is the trained machine-learning program 759. Various machine learning techniques may be used to train models to make predictions based on data fed into the models. During a learning phase, the models are developed against a training dataset of inputs to optimize the models to correctly predict the output for a given input. A training data set may be defined for desired functionality of the closed-loop algorithm and closed loop parameters may be defined for desired functionality of the closed-loop algorithm. Generally, the learning phase may be supervised, semi-supervised, or unsupervised; indicating a decreasing level to which the "correct" outputs are provided in correspondence to the training inputs. In a supervised learning phase, all of the outputs are provided to the model and the model is directed to develop a general rule or algorithm that maps the input to the output. In contrast, in an unsupervised learning phase, the desired output is not provided for the inputs so that the model may develop its own rules to discover relationships within the training dataset. In a semi-supervised learning phase, an incompletely labeled training set is provided, with some of the outputs known and some unknown for the training dataset.

Models may be run against a training dataset for several epochs (e.g., iterations), in which the training dataset is repeatedly fed into the model to refine its results. For example, in a supervised learning phase, a model is developed to predict the output for a given set of inputs, and is evaluated over several epochs to more reliably provide the output that is specified as corresponding to the given input for the greatest number of inputs for the training dataset. In another example, for an unsupervised learning phase, a model is developed to cluster the dataset into n groups, and is evaluated over several epochs as to how consistently it places a given input into a given group and how reliably it produces the n desired clusters across each epoch.

Once an epoch is run, the models are evaluated and the values of their variables are adjusted to attempt to better refine the model in an iterative fashion. In various aspects, the evaluations are biased against false negatives, biased against false positives, or evenly biased with respect to the overall accuracy of the model. The values may be adjusted in several ways depending on the machine learning technique used. For example, in a genetic or evolutionary algorithm, the values for the models that are most successful in predicting the desired outputs are used to develop values for models to use during the subsequent epoch, which may include random variation/mutation to provide additional data points. One of ordinary skill in the art will be familiar with several other machine learning algorithms that may be applied with the present disclosure, including linear regression, random forests, decision tree learning, neural networks, deep neural networks, etc.

New data 759 is provided as an input to the trained machine-learning program 422, and the trained machine-learning program 759 generates the assessment 756 as output. The outputted assessment 756 may be out of an expected range (e.g., anomalous), indicating that remedial action such as retraining 761 of the machine learning algorithm(s) is warranted. The system also may be configured to determine that the new data 760 includes anomalous data with respect to the training data 755 that was used to train the machine-learning program. The detection of new data that is anomalous may trigger remedial action(s) such as, if it is determined that the previously used training data is outdated, retraining 761 the machine learning program using updated training data.

Figure 8:
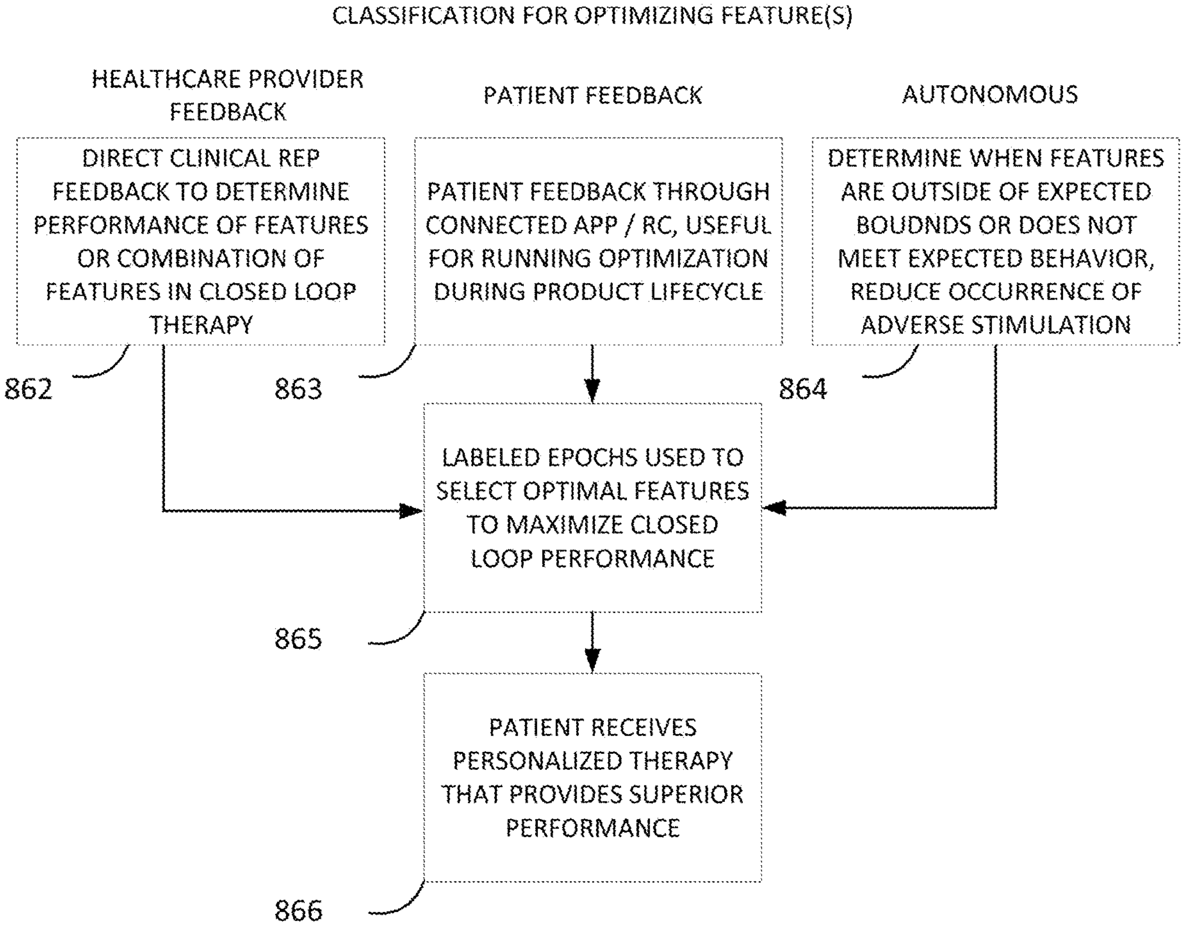
FIG. 8 illustrates, by way of example and not limitation, classification examples for optimizing features.

FIG. 8 illustrates, by way of example and not limitation, classification examples for optimizing features. These classifications may be used in a machine learning program. For example, the classifications may be based on feedback from a healthcare provider 862 such as a clinical rep, a physician or nurse, may be based on patient feedback 863, and/or may be autonomously determined 864. The healthcare provider may be directed to provide feedback to determine the performance of features or combination of features in a closed loop therapy. The patient may provide feedback through a remote control or an app on a personal device such as a phone to determine performance of features of combination of features for a closed loop therapy. The system may autonomously classify the output when the at least one of the plurality of available features is out of expected bounds meets or does not meet expected behavior during the delivery of the therapy, and may ack to reduce occurrence of adverse stimulation. The feedback may be used to label epochs, which may be used to select optimal feature from available features to maximize the closed-loop performance 865. As a result, the patient is able to receive a personalized therapy that provides a superior performance 866.

Figure 9:
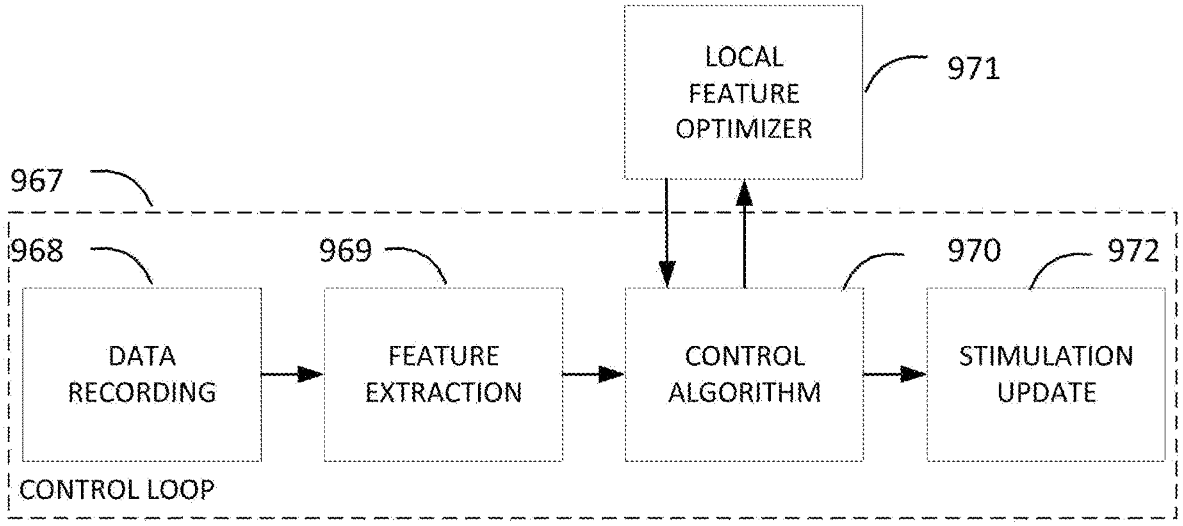
FIG. 9 illustrates, by way of example and not limitation, a control loop for locally optimizing closed-loop sensed feature(s) used to provide a closed-loop therapy.
Figure 11:
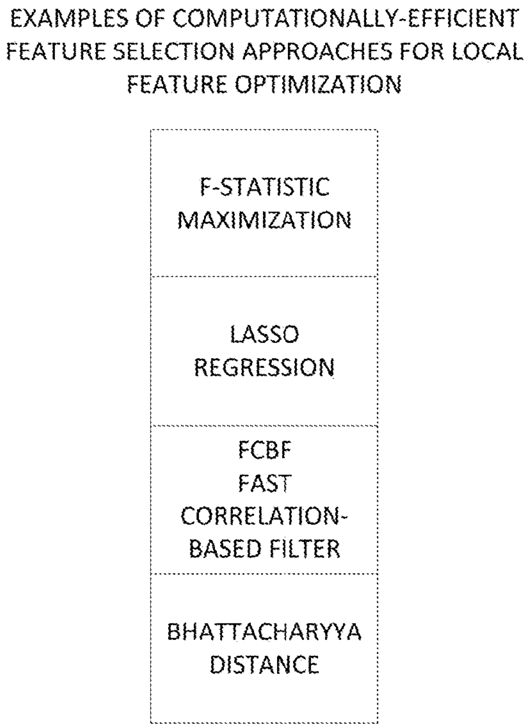
FIG. 11 illustrates, by way of example and not limitation, a few examples of computationally-efficient approaches that may be implemented by the local feature optimizer.

FIG. 9 illustrates, by way of example and not limitation, a control loop for locally optimizing closed-loop sensed feature(s) used to provide a closed-loop therapy. The control loop 967 generally includes data recording 968 (e.g., recorded signal data extracted from the sensed signal), and feature extraction 969 from the recorded signal. A control algorithm 970, in conjunction with a local feature optimizer 971, updates parameters of the stimulation based on the extracted features 972. The control loop may be performed autonomously within the firmware of the therapy device, performed on the order of each epoch or every N epochs. As it is implemented in the therapy, a relatively simple or computationally-efficient feature selection may be performed on the sensed data for a relatively small number of epochs. The epoch-to-epoch time may be on the order of ms to seconds. As illustrated in FIG. 11, examples of computationally-efficient approaches that may be implemented by the local feature optimizer include, but are not limited to, F-Statistic Maximization, Lasso regression, FCBF—Fast Correlation-Based Filter, and Bhattacharyya distance. The relatively term "computationally-efficient" referred to in FIG. 11 is in relation to the more complex methods illustrated in FIG. 12.

Figure 10:
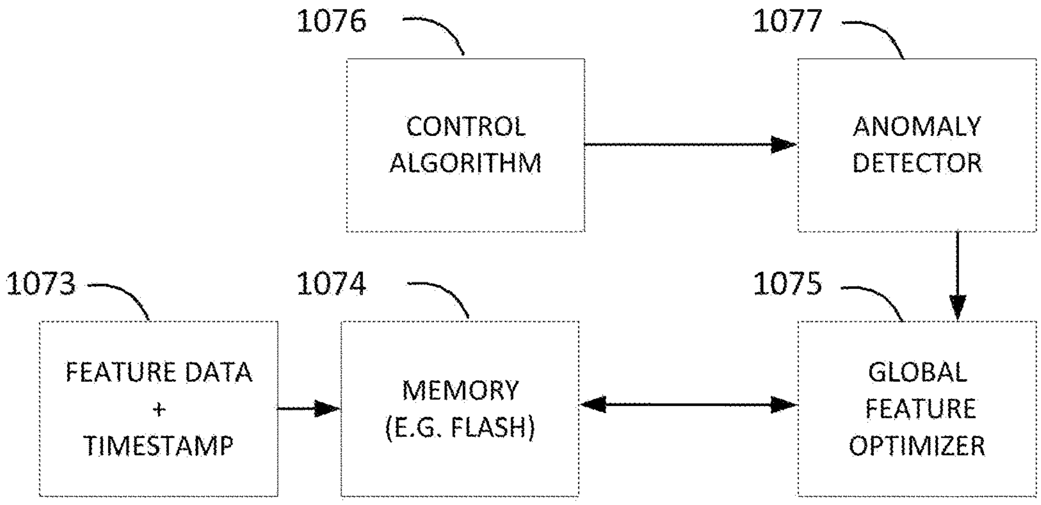
FIG. 10 illustrates, by way of example and not limitation, a process for retrospectively analyze previously-recorded data for globally optimizing feature(s) that may be used to provide a closed-loop therapy.

FIG. 10 illustrates, by way of example and not limitation, a process for retrospectively analyze previously-recorded data for globally optimizing feature(s) that may be used to provide a closed-loop therapy. Feature data and timestamps corresponding to the feature data 1073 may be stored in a memory 1074, such as a flash memory. The global feature optimization 1075 may be performed on feature data stored in the memory. The global feature optimization 1075 may be performed or as a periodic check. The period for performing the global optimization may be constant, may be variable, may be pre-programmed, or may be triggered by a user or sensed event. For example, the global optimization may be performed ever N days or weeks, or on-demand. For example, the global feature optimization may be performed in response to a detected anomaly. A control algorithm 1076 may implement an anomaly detector 1077. Upon detecting the anomaly, the system may perform the global feature optimization. For example, the system may enter a fallback mode when the anomalous data has been detected or anomalous outputs have been determined. The closed-loop therapy may be paused in response to the detected anomaly, or the therapy may change from being implemented in a closed-loop therapy to an open-loop therapy.

The detected anomaly may be detected feature value(s) that are greater than expected or less than expected. With respect to SCS, for example, the feature value(s) may be greater than expected when the lead moves closer to the spinal cord or when the impedance of sensing contacts increase, which may lead to the control algorithm reducing the stimulation amplitude. Furthermore, with respect to SCS for example, the feature value(s) may be less than expected when the lead moves further from the spinal cord or when the impedance of sensing contacts decrease, which may lead to the control algorithm increasing the stimulation amplitude.

The anomaly detector may perform statistical testing on extracted feature using expected min/max and variance, may compare the extracted feature with the stimulation amplitude for lower/upper bound checking, may store data on occurrences to detect trends, may activate a failure/fallback mode if the detected anomaly is significant, and may detect anomaly and/or performance degradation. The control algorithm may be re-parameterized to account for shift in setpoints (feature vs. stimulation relationship). This may be achieved via automated detection and message reporting through firmware. For example, a healthcare provider may receive the report, and then manually re-program the therapy device. This may involve troubleshooting with scripted action/questions with patient. An automated system may use "engineered features" with some randomization within safety bounds in order to discover new optimal features and improve patient experience over time. The control algorithm may access one or more of allowable stimulation parameters, minimum and maximum amplitude values, active stimulation parameters, expected minimum and maximum features, feature variance, feature value, and failure/fallback mode flags.

Figure 12:
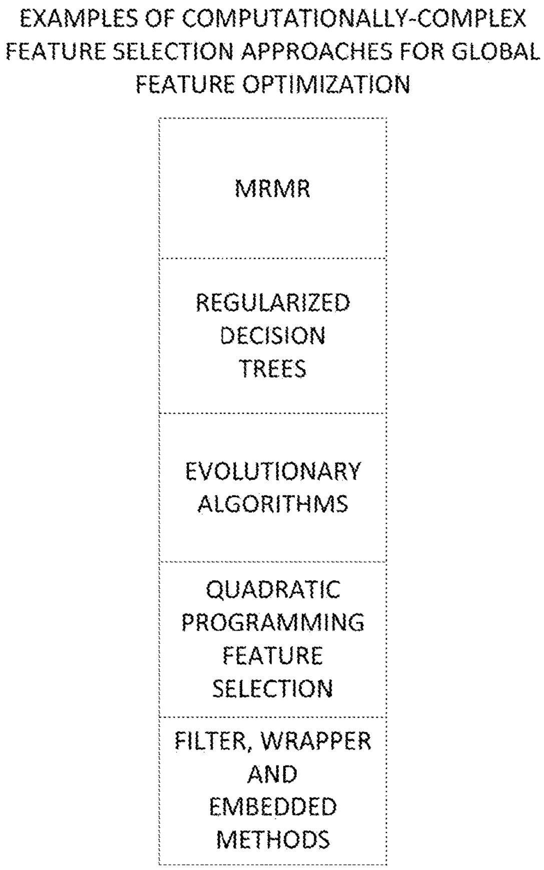
FIG. 12 illustrates, by way of example and not limitation, a few examples of computationally-complex approaches that may be implemented by the local feature optimizer.

The global optimization may use supervised or unsupervised learning on training data. As illustrated in FIG. 12, examples of computationally-complex approaches that may be implemented by the local feature optimizer include, but are not limited to, maximum relevance-minimum redundance (MRMR), regularized decision trees, evolutionary algorithms, quadratic programming feature selection, filter methods, wrapper methods, and embedded methods. A minimal-optimal methods seek to identify a small set of features that have the maximum possible predictive power. Regularized decision trees provide an algorithm that penalizes a given feature for being similar to other features. Filter methods suppress highly correlated features. Filter methods do not use a predictive model. Wrapper methods focus on iterations between features, using a predictive model algorithm to select features. Embedded methods combine the filter and wrapper methods. Embedded methods embed the feature selection process in the model is being built. Evolutionary algorithms may eliminate features through processes of crossover, mutation, and selection. Quadratic programming feature selection uses quadratic optimization (i.e., linear algebra) to solve for best features. The relative term "computationally-complex" referred to in FIG. 12 is in relation to the less complex methods illustrated in FIG. 11.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks or cassettes, removable optical disks (e.g., compact disks and digital video disks), memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method, comprising:

delivering a therapy to a patient, wherein the therapy is at least partially defined by a set of therapy parameters;

sensing a biological signal from the patient;

detecting a plurality of features of the biological signal to provide a plurality of detected features available for selection;

implementing a feature selection algorithm to evaluate the plurality of the detected features and determine a subset of the plurality of the detected features to be used as at least one closed-loop sensed feature; and implementing a feedback control algorithm, using the at least one closed-loop sensed feature, to control at least one therapy parameter in the set of therapy parameters.

2. The method of claim 1, wherein the therapy includes a neuromodulation therapy.

3. The method of claim 1, further comprising using at least one of hardware, firmware or ASICs within an implantable device to detect the plurality of features.

4. The method of claim 1, further comprising using software to detect the plurality of features.

5. The method of claim 1, further comprising using feedback from a healthcare provider or from the patient to implement the feature selection algorithm to determine at least one closed-loop sensed feature.

6. The method of claim 1, further comprising using sensed data to implement the feature selection algorithm to determine at least one closed-loop sensed feature.

7. The method of claim 6, wherein the sensed data includes at least one of the plurality of the detected features, and the method includes determining when the at least one of the plurality of the detected features meets or does not meet expected behavior during the delivery of the therapy.

8. The method of claim 1, wherein the implementing the feature selection algorithm includes autonomously running the feature selection algorithm within an implanted device to update the at least one closed-loop sensed feature for use by the feedback control algorithm to control the at least one therapy parameter.

9. The method of claim 8, wherein the feature selection algorithm includes at least one of: F-Statistic Maximization, Lasso Regression, Fast Correlation-Based Filter (FCBF) or Bhattacharyya Distance.

10. The method of claim 1, wherein the implementing the feature selection algorithm includes implementing the feature selection algorithm in an external device, in response to a trigger, to retrospectively analyze previously-recorded data.

11. The method of claim 10, wherein the trigger includes a user command or a detected feature anomaly during the therapy.

12. The method of claim 10, wherein the feature selection algorithm includes at least one of: MRMR, Regularized Decisions Trees, Evolutionary Algorithms, or Quadratic Programming Feature Sections.

13. The method of claim 10, wherein the feature selection algorithm includes at least one of: filter methods, wrapper methods or embedded methods.

14. A non-transitory machine-readable medium including instructions, which when executed by a machine, cause the machine to perform a method comprising:

delivering a therapy to a patient, wherein the therapy is at least partially defined by a set of therapy parameters;

sensing a biological signal from the patient;

detecting a plurality of features of the biological signal to provide a plurality of detected features available for selection;

implementing a feature selection algorithm to evaluate the plurality of the detected features and determine a subset of the plurality of the detected features to be used as at least one closed-loop sensed feature; and implementing a feedback control algorithm, using the at least one closed-loop sensed feature, to control at least one therapy parameter in the set of therapy parameters.

15. The non-transitory machine-readable medium of claim 14, wherein at least one of hardware, firmware or ASICs within an implantable device detects the plurality of features.

16. The non-transitory machine-readable medium of claim 14, wherein the method performed by the machine executing the instructions includes detecting the plurality of features.

17. The non-transitory machine-readable medium of claim 14, wherein the method further comprises using sensed data to implement the feature selection algorithm to determine at least one closed-loop sensed feature, wherein the sensed data includes at least one of the plurality of the detected features, and the method includes determining when the at least one of the plurality of the detected features meets or does not meet expected behavior during the delivery of the therapy.

18. The non-transitory machine-readable medium of claim 14, wherein the method further comprises using sensed data to implement the feature selection algorithm to determine at least one closed-loop sensed feature, including autonomously running the feature selection algorithm within an implanted device to update the at least one closed-loop sensed feature for use by the feedback control algorithm to control the at least one therapy parameter.

19. The non-transitory machine-readable medium of claim 14, wherein the implementing the feature selection algorithm includes implementing the feature selection algorithm in an external device, in response to a trigger, to retrospectively analyze previously-recorded data.

20. A system, comprising:

a therapy device configured to deliver a therapy to a patient, wherein the therapy is at least partially defined by a set of therapy parameters, wherein the therapy device includes sensing circuitry configured to sense a biological signal from the patient, and a closed-loop controller operably connected to the therapy device and the sensing circuitry, wherein the controller is configured to implement a feedback control algorithm to control the delivered therapy based on the sensed electrical signal by controlling at least one therapy parameter from the set of therapy parameters;

a feature detector configured to detect a plurality of features of the biological signal to provide a plurality of detected features available for selection; and a feature selection controller configured to implement a feature selection algorithm to evaluate the plurality of available features and determine a subset of the plurality of the detected features to be used as at least one closed-loop sensed feature from the plurality of available features, wherein the feedback control algorithm is configured to use the at least one closed-loop sensed feature to control the at least one therapy parameter.

* * * * *